United States Patent [19]

Tsuruoka et al.

[11] Patent Number: 4,961,345

[45] Date of Patent: Oct. 9, 1990

[54] VIBRATION TYPE TRANSDUCER

[75] Inventors: Michihiko Tsuruoka; Wataru Nakagawa; Masashi Machida; Naohiro Kounosu, all of Kanagawa, Japan

[73] Assignee: Fuji Electric Co., Ltd., Kanagawa, Japan

[21] Appl. No.: 129,521

[22] Filed: Dec. 7, 1987

[30] Foreign Application Priority Data

Dec. 8, 1986 [JP] Japan .................................. 61-291968
Dec. 17, 1986 [JP] Japan .................................. 61-300274
Mar. 30, 1987 [JP] Japan .................................. 62-77264
Apr. 24, 1987 [JP] Japan .................................. 62-101625

[51] Int. Cl.[5] .............................................. G01L 9/08
[52] U.S. Cl. ................................................... 73/32 A
[58] Field of Search .............. 73/579, 32 A, 702, 704, 73/721, 727, 862.59; 310/324, 338

[56] References Cited

U.S. PATENT DOCUMENTS 4,435,986 3/1984 Choffat ................................ 73/702
4,644,804 2/1987 Ramm et al. ....................... 310/338

FOREIGN PATENT DOCUMENTS 5961777 10/1985 Japan .................................... 73/727
139786 6/1986 Japan .

OTHER PUBLICATIONS

Japanese Patent Application No. 139786/86; filed 6/16/86 by Tsuruoka et al.

Primary Examiner—Hezron E. Williams
Assistant Examiner—Louis M. Arana
Attorney, Agent, or Firm—Finnegan, Henderson, Farabow, Garrett, and Dunner

[57] ABSTRACT

The apparatus of the present invention detects the resonant frequency of a vibratory member in contact with the fluid in order to determine the density or pressure of the fluid. The vibratory member is disposed in a housing to form a cavity with no flow communication between the side of the vibratory member facing into the cavity and the other side of the vibratory member. The vibratory member is vibrated by an annular piezoelectric device which may be attached to one or both sides of the vibratory member. An amplifier and feedback circuit regulate the frequency of oscillation of the piezoelectric device to that of the resonant frequency. The piezoelectric device may be comprised of several separate sections or several sections with partial interruptions in the piezoelectric material. Instead of the vibratory member and the piezoelectric transducer combination, the vibratory member may be constructed from a single fixed piezoelectric device with another piezoelectric disc mounted thereon. In this configuration one of the devices is used to mechanically excite the other and through a feedback circuit establish the resonant frequency of the two laminated piezoelectric devices.

5 Claims, 9 Drawing Sheets

VIBRATION TYPE TRANSDUCER

BACKGROUND OF THE INVENTION

The present invention relates to a vibration type transducer for measuring a density or a pressure of a fluid to be measured by detecting a resonant frequency of a vibratory plate which is in contact with the fluid.

The present inventors have proposed a vibration type transducer disclosed in Japanese Patent Publication No. 239228/1985 and U.S. patent application Ser. No. 922,694 now U.S. Pat. No. 4,872,335 which measures the density or the pressure of the fluid by utilizing the relationship wherein a resonant frequency of a composite vibration system varies in accordance with an inertance at a fluid introducing port, i.e., depending on the density of the fluid to be measured. This composite vibration system is composed of a disk-like mechanical vibration part and an acoustic vibration system including a cavity contactually formed in at least one surface of the mechanical vibration part and the fluid introducing port for introducing the fluid into the cavity.

Figure 1:
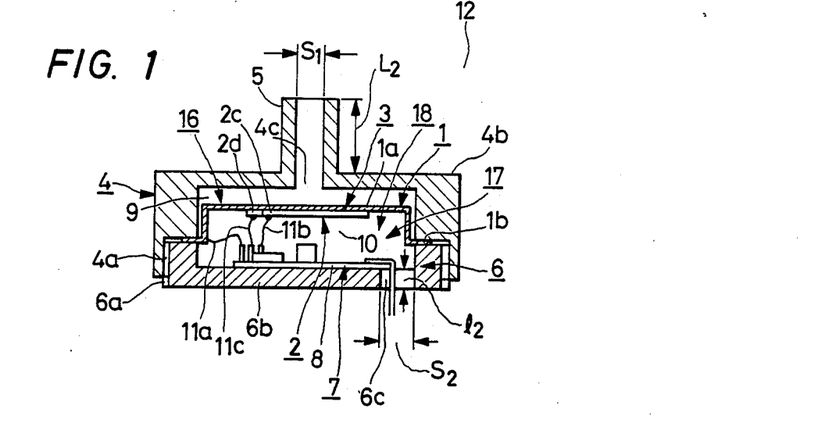
FIG. 1 is a longitudinal cross-sectional view of a vibratory transducer related to the present invention.
Figure 2:
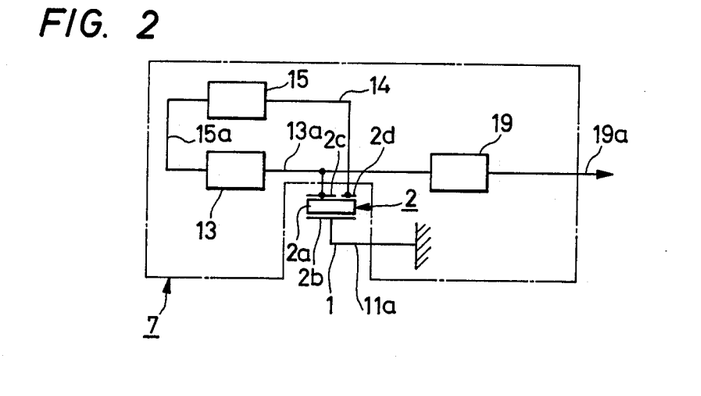
FIG. 2 is a schematic diagram of the control circuit and transducer of the vibratory transducer of FIG. 1.

FIG. 1 is a longitudinal cross-sectional view illustrating the principal portion of a vibration type transducer associated with the above-mentioned proposal. FIG. 2 is a block diagram of the transducer depicted in FIG. 1. In FIGS. 1 and 2, a vibratory member with a cylindrical bottom, generally indicated at 1, is constructed such that a disk-like piezoelectric vibrator 2 is fixedly bonded to an inner surface of a bottom 1a, and an opening end is provided with a collar 1b. The vibratory member 1 is formed of a metal thin film which is approximately 0.1 mm in thickness. The piezoelectric vibrator 2 is constituted by a disk-like piezoelectric substrate 2a having a thickness of approximately 0.2 mm, a first electrode 2b formed on one surface of the substrate 2a, a second electrode 2c and a third electrode 2d which are formed on the other surface of the substrate 2a. The surface of the substrate 2a on which the first electrode 2b is disposed is attached to the bottom 1a of the vibratory member 1. The electrode 2b is electrically connected to the vibratory member 1.

The reference numeral 3 designates a mechanical vibration part consisting of the cylindrical vibratory member 1 and the piezoelectric vibrator 2. The numeral 4 represents a cylindrical bottomed container including a female thread 4a formed in the opening end thereof. One end of a cylindrical tube 5 is fixed to an outer surface of a bottom 4b of this container. The bottom 4b of the container is formed with a circular through-hole 4c through which the inside of the tube 5 communicates with the inside of the container 4. The through-hole 4c has a diameter equal to the inside diameter of the tube 5.

The numeral 6 denotes a cylindrical bottom housing designed for fixing the vibratory member 1. The collar 1b is sandwiched in between the container 4 and the housing 6 by causing a male thread 6a formed on an outer surface of the housing 6 to screw into the female thread 4a, thus fixing the vibratory member 1. A bottom 6b of the housing 6 is formed with a through-hole 6c. A printed circuit substrate 8 constituting of a detecting circuit 7 is fixedly bonded to an inner surface of the bottom 6c. A first cavity generally designated at 9 is surrounded by the vibratory member 1 and the housing 6. The cavities 9 and 10 are partitioned by the vibratory member 1 so as to have a high density of fluid. The symbols 11b and 11c denote conductors through which the electrodes 2c and 2d of the piezoelectric vibrator 2 and the vibratory member 1 are connected to the detecting circuit 7.

Next, the operation of the transducer illustrated in FIG. 1 will be explained. To start with, the transducer is placed in a fluid 12 to be measured. The fluid 12 flows via the tube 5 into the cavity 9 and via the through-hole 6c into the cavity 10. Immediately when the detecting circuit 7 is charged with the electricity, an AC voltage 13a is outputted from AC amplifier 13. The voltage 13a is impressed on the second electrode 2c of the piezoelectric vibrator 2. The piezoelectric substrate 2a is arranged to expand and contract in the radial direction, depending on the positive and negative of the voltage 13a. As a result, the bottom 1a of the vibratory member 1 performs flexural vibrations in the axial direction of the tube 5 of the vibratory member. An AC voltage on line 14 is produced corresponding to distortion of the piezoelectric substrate 2a between the first electrode 2b and the third electrode 2d of the vibrator 2. This voltage on line 14 is input to a feedback circuit 15 which effects a positive feedback of an output voltage on line 15a to the AC amplifier 13.

It follows that the bottom 1a of the vibratory member performs self-oscillations while maintaining a flexural vibration state in which the resonance takes place at the natural oscillation frequency F of a composite vibration system 18 consisting of: a first acoustic vibration system 16 formed by the first cavity 9, the through-hole 4c and the internal portion of the tube 5, this vibration system 16 is based on the fluid 12 introduced into a communication space; the mechanical vibratory part 3; and a second acoustic vibration system 17 formed by the second cavity 10 and the through-hole 6c, this vibration system 17 being based on the fluid 12 introduced into the communication space. In this case, the oscillation frequency F corresponds, as will be discussed below to a density $\rho$ of the fluid 12 to be measured and further accords with a frequency of the AC voltage on line 13a. The density $\rho$ can therefore be measured by obtaining the frequency of the output voltage on line 13a. An output circuit generally indicated at 19 receives the input of the voltage 13a and is intended to facilitate the measurement of the oscillation frequency F by outputting a pulse train signal 19a having a pulse frequency identical with the frequency of the voltage 13a. The detecting circuit 7 comprises the amplifier 13, the feedback circuit 15 and the output circuit 19.

Figure 3:
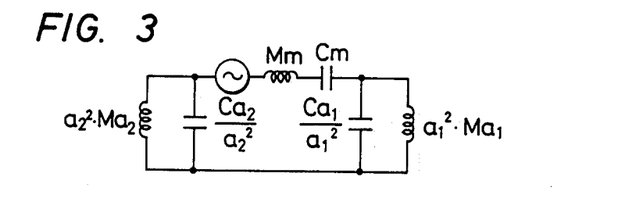
FIG. 3 is an equivalent circuit diagram of the operation of the vibratory transducer of FIG. 1.

Next, the fact that the oscillation frequency F is a function of the density $\rho$ will be explained. The transducer depicted in FIG. 1 is, as explained earlier, defined as the composite vibration system consisting of the mechanical vibration part 3 serving as a mechanical vibration system, the first acoustic vibration system 16 and the second acoustic vibration system 17. As illustrated in FIG. 3, an electrical equivalent circuit illustrates how the vibration system 18 converts the acoustic vibration system 16 and 17 into the mechanical vibration system. In FIG. 3, the symbols Mm and Cm respectively denote an effective mass and a compliance of the vibration part 3; the symbol $M_{a1}$ represents an inertance of the fluild 12 in the tube 5 $C_{a1}$ stands for an acoustic capacity of the fluid 12 within the first cavity 9; $M_{a2}$ designates an inertance of the fluid 12 in the through-hole 6c; and $C_{a2}$ denotes an acoustic capacity of the fluid 12 within the second cavity 10. The symbols $a_1$ and $a_2$ indicate the conversion coefficient for converting individual constants for the acoustic vibration of the mechanical vibration system. The above-mentioned acoustic capacities $C_{a1}$ and $C_{a2}$, and the inertances $M_{a1}$ and $M_{a2}$ are expressed in the following formulae (1) and (2).

$$C_{a1} = V_1/(\rho C^2), \quad M_{a1} = (\rho l_1)/S_1 \tag{1}$$

$$C_{a2} = V_2/(\rho C^2), \quad M_{a2} = (\rho l_1)/S_2 \tag{2}$$

where $V_1$ and $V_2$ are the volumes of the cavities 9 and 10; c is the sound velocity; $l_1$ and $S_1$ are the length and the sectional area, respectively, of the tube 5; and $l_2$ and $S_2$ are the length and the sectional area, respectively, of the through-hole 6.

FIG. 3 explains the transducer illustrated in FIG. 1. The acoustic capacity $C_{a2}$ is made to increase, whereas the inertance $M_{a2}$ is made to decrease. The principal portion of the transducer is constructed so that a resonant frequency $F_{a2}$ of the vibration system which is composed of $C_{a2}$ and $M_{a2}$ is considerably lower than a resonant frequency Fm of the vibration system which is composed of Cm and Mm. Hence, FIG. 3 is redrawn into FIG. 4.

Figure 4:
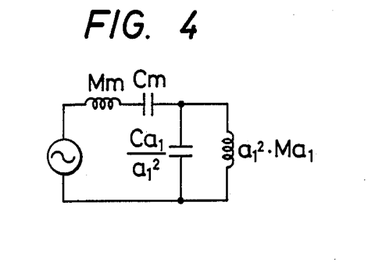
FIG. 4 is an equivalent circuit diagram derived from approximations applied to FIG. 3.
Figure 5:
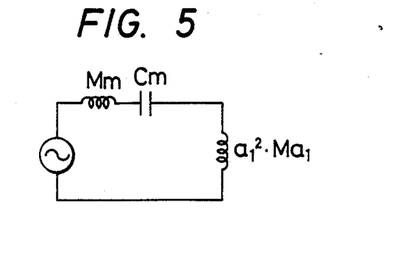
FIG. 5 is an equivalent circuit diagram derived from approximations applied to FIG. 4.

FIG. 4 is redrawn into FIG. 5 where an acoustic compliance $(_{ca1}/a_1^2)$ and an acoustic mass $(a_1^2 \cdot M_{a1})$ are selected to establish formula (4) with respect to an angular frequency $\omega_n$ expressed by the formula (3). As is obvious from FIG. 5, $\omega_n$ is the resonant angular frequency of the circuit depicted in FIG. 5.

$$\omega_n^2 = [1/(Cm \cdot (Mm + a_1^2 \cdot M_{a1}))] \tag{3}$$

$$1/(\omega_n \cdot (C_{a1}/a_1^2)) >> \omega_n (a_1^2 \cdot M_{a1}) \tag{4}$$

The formula (5) is obtained from the formulae (3) and (4). However, for sufficient sensitivity in measurement of the density, it is usually required to establish the conditions of formula (6). Therefore, the formula (7) is deduced from the formulae (5) and (6) as follows:

$$\frac{-1}{(c_{a1}/a_1^2) \cdot (a_1^2 \cdot M_{a1})} \quad \frac{1}{Cm(mm + a_1^2 \cdot M_{a1})} \tag{5}$$

$$a_1^2 \cdot M_{a1} \approx Mm \tag{6}$$

$$Cm >> (C_{a1}/a_1^2) \tag{7}$$

The principal portion of the transducer illustrated in FIG. 1 is constructed to make the formulae (6) and (7) valid. Consequently, the formula (4) is established through the formula (5). In this case, the electrical equivalent circuit of the composite vibration system is therefore expressed in FIG. 5. It follows that the vibration system 18 continues the self-oscillations at the resonant frequency F corresponding to $\omega_n$ of the formula (3). However, it is evident from the formulae (1) and (3) that $\omega_n$ is the function of the density $\rho$. Therefore, in the transducer depicted in FIGS. 1 and 2, the density $\rho$ of the fluid 13 can be measured on the basis of the pulse frequency of the signal 19a outputted from the detecting circuit 7.

The transducer illustrated in FIG. 1 has an advantage in that the density can be measured with the above-described simple apparatus. However, the effective mass Mm of the mechanical vibration part 3 increases because the piezoelectric vibrator 2 has a disk-like configuration. As can be understood from the formula (3), this creates a problem wherein the sensitivity in measurement of the density is low.

SUMMARY OF THE INVENTION

Accordingly, it is a primary object of the present invention to enhance the sensitivity in measurement of the density by diminishing the effective mass Mm of the mechanical vibration part 3.

To achieve the objects and in accordance with the purpose of the invention, as embodied herein, the apparatus for detecting the resonant frequency of a vibratory member in contact with a fluid comprises a housing having an interior chamber, a substantially planar vibratory member mounted to vibrate in the housing, the member having opposite first and second sides and disposed in the interior chamber of the housing to define a first and second cavity and prevent flow communication between said first and second cavities, a first fluid inlet means for introducing a fluid into the first chamber and resonant frequency detection means responsive to the fluid contact and associated with the vibratory member for detecting the resonant frequency of the vibratory member, the resonant frequency detection means includes an annular transducer mounted to the vibratory member.

In accordance with another aspect of the invention, as embodied and broadly described herein, the apparatus for detecting the resonant frequency of a vibratory member in contact with a fluid of this invention comprises a housing having an interior chamber, a vibratory member having a first and second side mounted in the housing, the vibratory member disposed in the interior chamber to define a first internal cavity and to prevent flow communication of fluid between the first side of the vibratory member to the second side, a first fluid inlet means for introducing a fluid into the first chamber, a vibratory controller for controlling and responding to the vibratory member and the vibratory member further including a first fixedly held substantially planar piezoelectric device and a second substantially planar piezoelectric device secured together in planar relationship.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIGS. 6B1–6B3 illustrate the vibrator of FIG. 6A;

FIGS. 9B1 and 9B2 illustrate the top surface and underside of a vibrator illustrated in FIG. 9A, respectively;

DESCRIPTION OF THE PREFERRED EMBODIMENTS

Reference will now be made in detail to the present preferred embodiment of the invention, an example of which is illustrated in the accompanying drawings.

Figure 6:
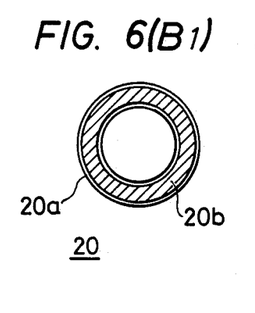
FIG. 6A is a longitudinal cross-sectional view of a first embodiment of the vibratory transducer of the present invention.
Figure 6A:
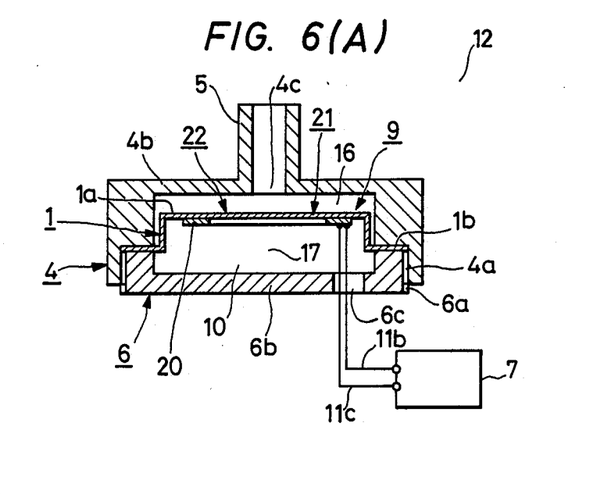

As shown in FIG. 6(A), there is illustrated a longitudinal sectional view of a first embodiment of the present invention. Referring to FIG. 6(A) as compared with FIG. 1, a detecting circuit 7 is placed outside a second cavity 10, and a piezoelectric vibrator corresponding to a piezoelectric vibrator 2 shown in FIG. 1 is, as illustrated in FIGS. 6(B1) through 6(B3), formed in a ring-like shape FIGS. 6(B1), 6(B2) and 6(B3) are views respectively illustrating the underside, the side face and the top surface of a vibrator 20.

As shown in FIGS. 6B1–6B3, the vibrator 20 is composed of: an annular plate-like substrate 20a formed from ceramic, such as a PZT system, this substrate 20a has a thickness of approximately 0.05 mm to 0.2 mm; a first electrode 20b assuming a flat annular configuration which is provided on the underside of the substrate 20a; a second electrode 20c formed on the top surface of the substrate 20a, the second electrode 20c including a notch formed in a part of the surface; and a third electrode 20d provided in the notch formed in the surface of the substrate 20a. The electrode 20b and 20c are so disposed as to be concentric with the substrate 20a.

The vibrator 20 is fixed to the bottom 1a of a vibratory member 1 in such a way that the electrode 20b is electrically connected to the inner surface of bottom 1a. Preferably, attachment involves the use of a conductive epoxy adhesive agent mixed with, for instance, silver particles In this case, the vibratory member 1 is formed from an alloy of iron and nickel and is about 0.05 mm to 0.1 mm in thickness. This alloy should have a coefficient of thermal expansion which is roughly equal to that of the piezoelectric vibrator 20 so as not to produce deformation in the bottom 1a which is due to a difference in coefficient of thermal expansion between the vibratory member 1 and the vibrator 20. The numeral 21 denotes a mechanical vibration part composed of the vibrator 20 and the vibratory member 1.

In FIG. 6, the vibrator 20 is constructed in the above-mentioned manner, and hence the mass of the mechanical vibration part 21 is smaller than that of the mechanical vibration part 3 depicted in FIG. 1 which employs the disk-like piezoelectric vibrator 2 which has the same outside diameter and the same thickness vibrator 20 instead of the vibrator 20. From formula (3), the resonant frequency of a composite vibration system 22 shown in FIG. 6, which corresponds to the composite vibration system 18 shown in FIG. 1, is higher than that of the composite vibration system 18 where the detecting circuit 7 is disposed inside the cavity 10. It can also be understood from formula (3) that a variation rate of the resonant frequency of the composite vibration system 22 with respect to the density $\rho$ of a fluid 12 to be measured is greater than that in the composite vibration system 18. The sensitivity in the measurement of density is higher in the transducer depicted in FIG. 6 than in the transducer illustrated in FIG. 1.

Figure 7:
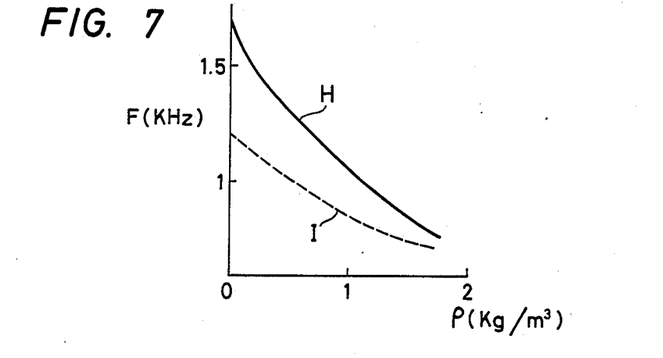
FIG. 7 is a graph illustrating the relationship between density of a fluid and the resonant frequency of a vibration system for the vibration systems illustrated in FIGS. 1 and 6, respectively.

FIG. 7 is a graph illustrating the results of an experiment confirming the above-described characteristics. FIG. 7 illustrates a relation between the density $\rho$ of the fluid 12 and the resonant frequency F of the composite vibration systems 18 and 22, the frequency F varying in accordance with the density $\rho$. The symbol H indicates a characteristic line when using the vibrator 20, and I is the characteristic line when using the vibrator 2. These characteristic lines are obtained from the results of the experiment performed on condition that all the element constants in the vibration systems 18 and 22 are the same except for the configurations of the vibrators 2 and 20. It can be observed from FIG. 7 that if the vibrator assumes a ring-like configuration, the resonant frequency F increases, and the sensitivity in measurement of the density is also enhanced.

Figure 8A:
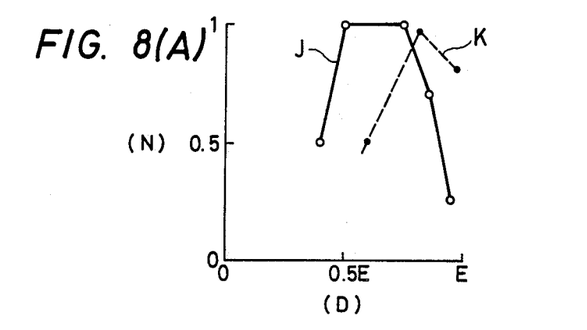
FIGS. 8A and 8B illustrate the relationship between the displacement of the bottom of a vibratory member and the outside diameter of an attached vibrator; and the dimensions of the transducer vibratory member and vibrator respectively.
Figure 8B:
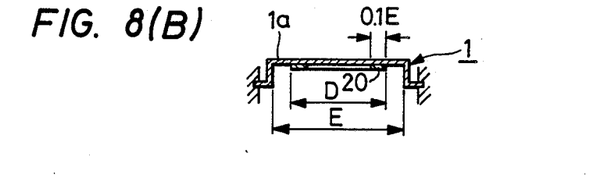

In FIG. 6, the driving force which causes the flexural vibrations of the bottom 1a of the vibratory member 1 cause expansion and contraction in the radial direction of the piezoelectric vibrator 20. Hence, the driving forces acting on the bottom 1a are small when vibrator 20 is used as compared with a case where the disk-like vibrator 2 is employed, and it follows that an amplitude of vibration of the bottom 1a decreases On the other hand, the flexural rigidity of bottom 1a when using the annular plate-like vibrator 20 is smaller than when employing the vibrator 2. A decrease in flexural rigidity causes an increase in the amplitude of vibration of bottom 1a. FIG. 8A is an explanatory graph showing results of an experiment based on this relationship In FIG. 8(B), E is defined as an inside diameter of the vibratory member 1, D is defined as an outside diameter of the vibrator 20, and 0.1 E indicates a width of a circular ring of the vibrator 20. In FIG. 8(A), a characteristic line J indicates a relation between a displacement N in the central portion of the bottom 1a and the outside diameter D of vibrator 20 when varying this outside diameter D; and a characteristic line K illustrates a relation between the outside diameter D of vibrator 2 and the displacement N in the central portion of the bottom 1a when making use of vibrator 2 in the transducer depicted in FIG. 6 in place of vibrator 20. As is apparent from FIG. 8(A), in the case of vibrator 20 the displacement N reaches the maximum value when D=0.5E to 0.7E. This maximum value is substantially equal to or slightly greater than the maximum value in the case of the vibrator 2. In FIG. 8(A) it can be seen that when the piezoelectric vibrator assumes the ring-like configuration, the bottom 1a does not decrease in amplitude but instead the amplitude of vibration of the bottom 1a is greater than that in the case of using the disk-like vibrator.

In formula (3), variation in the resonant frequency of the composite vibration system 22 shown in FIG. 6 depends on the compliance Cm of the mechanical vibration part 21. The compliance Cm is equivalent to the flexural rigidity in the vibration part 21 which varies in accordance with dimensions and qualities of the individual components of the vibration part 21 as well as physical properties of an adhesive agent between the bottom 1a and the vibrator 20. During manufacture of mechanical vibration parts 21 in quantity it is necessary to make the compliance Cm uniform by minimizing unevenness in thickness of the adhesive agent and presence of air bubbles therein. In FIG. 6 the vibrator 20 is formed in the ring-like shape, and a contactual area of the vibrator 20 with respect to the bottom 1a of the vibration part is small. Therefore, when manufacturing a multiplicity of mechanical vibration parts 21, viz., a large number of transducers, it is feasible to reduce the unevenness in thickness of the adhesive agent and presence of the air bubbles therein. This facilitates the uniformity of the compliance Cm when the ring-like piezoelectric vibrator 20 is used, since the area of vibrator 20 which contacts bottom 1a of the vibratory member via the adhesive agent is small. The flexural rigidity of the mechanical vibration part 21 is determined mainly by the dimensions and composition of the vibratory member 1 which results in the uniformity of the thermal properties of the transducer.

Figure 9A:
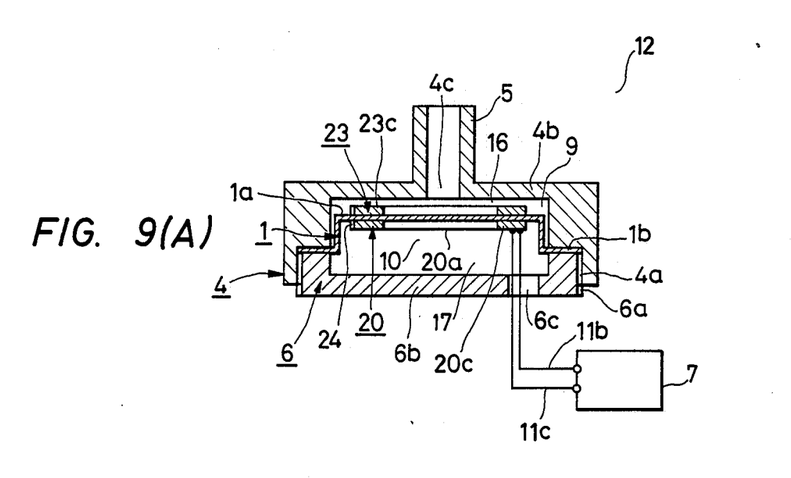
FIG. 9A is a longitudinal cross-sectional view of a second embodiment of the vibratory transducer of the present invention.
Figure 9B:
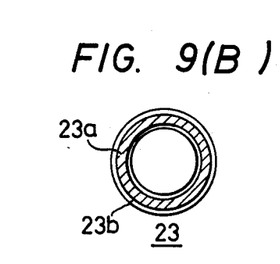

FIGS. 9(A), 9(B1) and (B2) are explanatory views illustrating a second embodiment of the present invention FIG. 9(A) is a longitudinal cross-sectional view of the transducer FIGS. 9(B1) and 9(B2) are views illustrating the top surface and underside of a piezoelectric vibrator 23 shown in FIG. 9(A). FIG. 9(A) is different from FIG. 6(A) in that a second piezoelectric vibrator 23 is fixedly bonded to the bottom 1a of the vibratory member on the side of the cavity 9 in contrast to the piezoelectric vibrator 20 provided on the side of cavity 10 of the first embodiment.

In FIGS. 9(B1) and 9(B2), the vibrator 23 consists of: an annular substrate 23a formed from the same piezoelectric material and with the same dimensions as those of the substrate 20a of the vibrator 20; a first annular film-like electrode 23b concentrically formed on the underside of the substrate 23a; and a second annular film-like electrode 23c concentrically formed on the surface of the substrate 23a. The first electrode 23b is so fixed to the bottom 1a of the vibratory member as to be electrically connected to this bottom 1a. The second electrode 23c of the vibrator 23 is connected through a lead wire 24 to the second electrode 20c of the vibrator 20 to keep airtightness between the cavities 9 and 10.

The transducer depicted in FIG. 9(A) is constructed in the above-described manner so that the density can be measured with high sensitivity as in the case of the transducer shown in FIG. 6(A) In FIG. 9(A) the vibrator 20 and the vibrator 23 cooperate to drive the bottom 1a of the vibratory member. Consequently, it is possible to operate these vibrators 20 and 23 at lower voltages than vibrator 2 in FIG. 6(A). In FIG. 9(A), the bottom 1a of the vibratory member is driven from both sides by the piezoelectric vibrators 20 and 23, thereby preventing thermal deformation due to a difference in coefficient of thermal expansion between the bottom 1a and the vibrators 20 and 23. Hence, the uniformity in thermal characteristics of the transducer is improved.

The above-described embodiment adopts the PZT ceramic as a material from which the substrate of the piezoelectric vibrator is formed. In the present invention, however, the substance may involve the use of monocrystalline ZnO. It is also possible to use a magnetostrictive material which is employed for the substrate instead of the piezoelectric material.

Figure 10A:
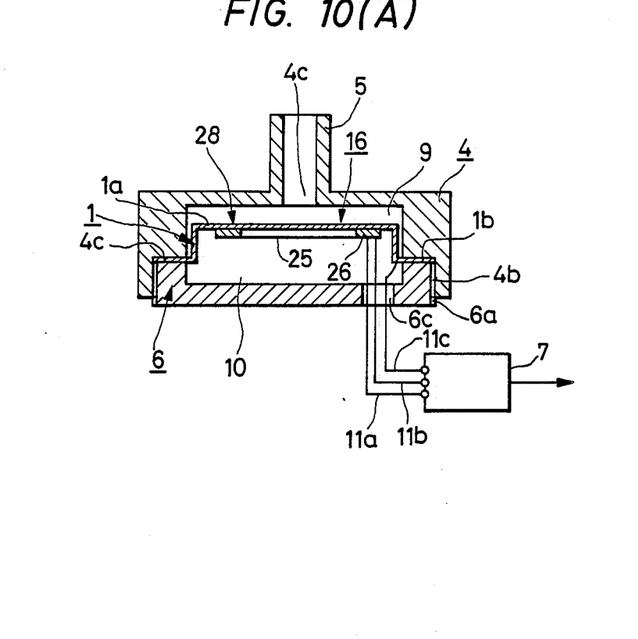
FIGS. 10A and 10B illustrate respectively a longitudinal cross-sectional view illustrating a third embodiment of the present invention and a top view illustrating the principal portion thereof.
Figure 10B:
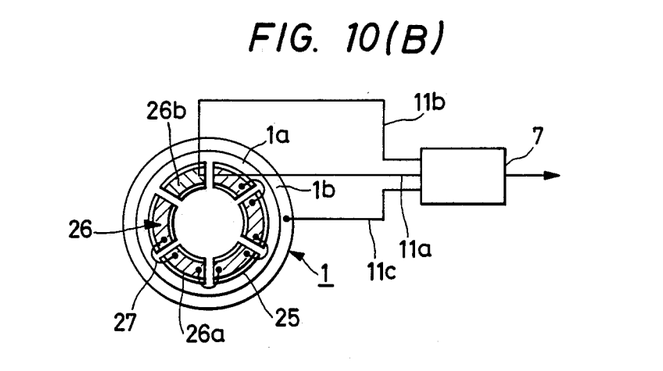
Figure 11A:
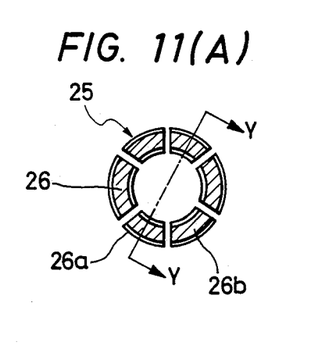
FIG. 11 is a view of the vibrator used in the vibratory transducer of FIG. 10.
Figure 11B:
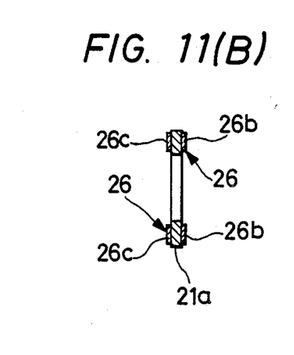

Referring to FIG. 10, there is illustrated a third embodiment of the present invention. FIG. 10(B) is an explanatory view showing the principal portion of the vibration type transducer, and FIG. 10(A) is a longitudinal cross-sectional view illustrating a construction of the principal portion in the third embodiment of the present invention. FIG. 11 is a view showing a construction of the vibrator depicted in FIG. 10; FIG. 11(A) is a plan view thereof; and FIG. 11(B) is a sectional view taken substantially along the line Y—Y of FIG. 11(A).

In FIGS. 10 and 11, the main difference from the vibration type transducer shown in FIGS. 6 through 9 is that a vibrator 25 corresponding to the piezoelectric vibrator 20 is provided for producing flexual vibrations in the bottom 1a of the vibratory member. The vibrator 25 is formed in such a way that six pieces of split piezoelectric elements 26 each assuming a circular arc configuration are annularly disposed on the inner surface of the bottom 1a of the vibratory member so as to be concentric with respect to the center of the bottom surface. Each of the split piezoelectric elements 26 consists of a circular arc piezoelectric substrate 26a formed from the piezoelectric material and electrodes 26b and 26c which are respectively formed on the top surface and on the underside of the substrate.

The electrode 26c is attached to the bottom 1a of the vibratory member with a conductive adhesive agent to form an electrical contact between electrode 26c and bottom 1a. The numeral 27 designates a connecting wire for connecting the electrodes 26b of the contiguous split ring of piezoelectric vibrators 26. In the vibrator 25, five pieces of electrodes 26b are connected by the connecting wires 27 to have the same potential and further connected through a lead wire 11a to the detecting circuit 7; and the remaining electrode is connected through a lead wire 11b to the detecting circuit 7. In the transducer illustrated in FIG. 10, the vibratory member 1 is connected through a lead wire 11c to the detecting circuit 7. The piezoelectric material from which the piezoelectric substrate 26a is formed involves the use of a piezoelectric ceramic of Pb (ZrTi) $O_3$ system, but ZnO ceramic may also be used. A mechanical vibration part generally indicated at 28 is composed of the vibrator 25, the connecting wire 22 and the vibratory member 1.

In the vibration type transducer depicted in FIG. 10, the flexural vibrations of the bottom 1a of the vibratory member are caused by five pieces split piezoelectric elements 26 unlike the arrangement of FIG. 6 in which the vibrations are caused by an annular piezoelectric vibrator 20. Consequently, the forces of thermal deformation with respect to the mechanical vibration part 28 are apparently smaller than the forces of thermal deformation which similarly act on the mechanical vibration part 21 shown in FIG. 6. The forces of thermal deformation on mechanical vibration part 28 are produced by a difference in the coefficients of thermal expansion between the split piezoelectric elements 26 and the bottom 1a of the vibratory member and a variation in temperature of the fluid 12 to be measured Where the vibration type transducer is constructed in the manner described in FIGS. 10, 11A and 11B, the thermal deformation created in the mechanical vibration part 28 becomes small as compared with that in the embodiment of FIG. 6. In consequence, an error in the measurement results due to temperature variations is reduced.

Figure 12:
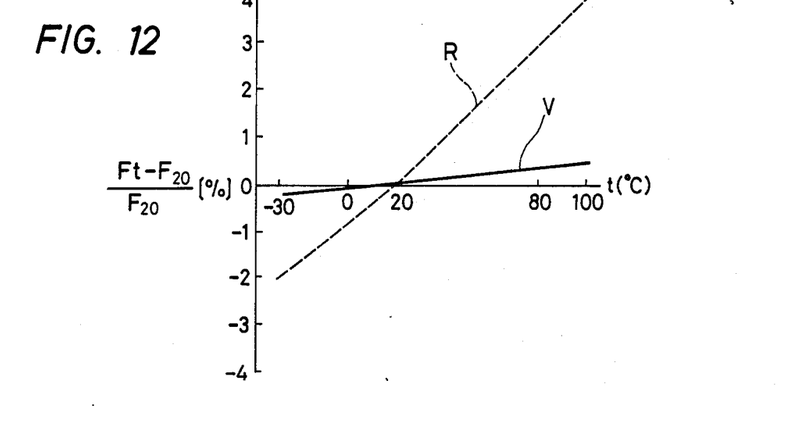
FIG. 12 is a graph of frequency change versus temperature for an experiment conducted with two different embodiments of the vibrator.

FIG. 12 is an explanatory graph showing results of experiments performed on a device R wherein the cavity 9 of the transducer shown in FIG. 6 into an open state by removing container bottom 4b and tube 5 and on a device V the cavity 9 of the transducer illustrated in FIG. 10 was put into the same way. FIG. 12 is created by measuring both a frequency $F_{20}$ of the flexural vibrations of the mechanical vibration parts 21 and 28 which are resonated in devices R and V, respectively, in the air at a temperature of 20° C. and a frequency Ft of the flexural vibrations thereof under the same conditions except that the temperature is t° C. It can be understood from FIG. 12 that the transducer which employs the split piezoelectric vibrators 26 exhibits a smaller error due to temperature variations than the other type of transducer which uses a single annular piezoelectric vibrator. This experiment is performed under conditions where each of the devices R and V is arranged such that the inside diameter of the bottom 1a of the vibratory member is 24 mm, the outside diameter of the vibrator is 23 mm, and the inside diameter of the vibrator is 18 mm.

Figure 13:
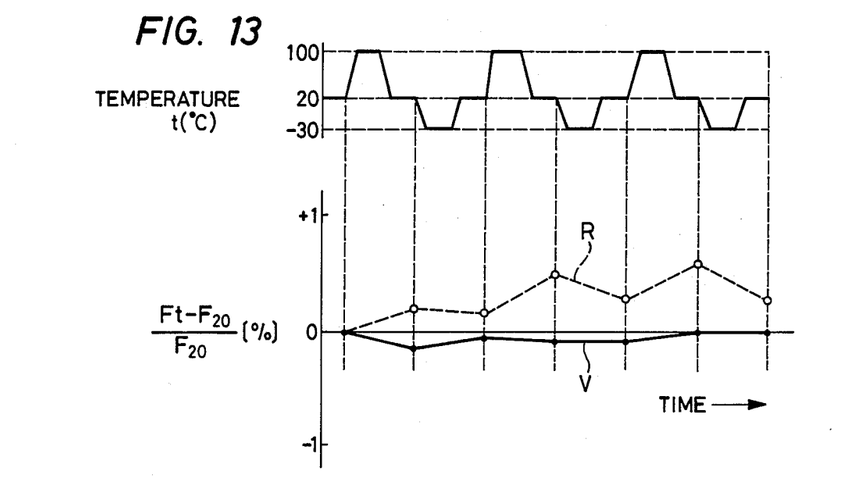
FIG. 13 is a graph of frequency change over time during conditions of varying temperature for the same two vibrators compared in FIG. 12.

FIG. 13 is an explanatory graph showing the results of a different experiment from that of FIG. 12. In this experiment, the devices R and V are left in air which undergoes temperature changes over time as illustrated in the FIG. 13. Subsequently, the results are obtained by measuring the frequencies of the flexural vibrations identical with those in FIG. 12 at the points shown in the Figure. $F_{20}$ and Ft shown in FIG. 13 are the same in concept as those in FIG. 12. As is apparent from FIG. 13, where the split piezoelectric vibrators 26 are employed, the temperature-error in measuring the density and the pressure is small.

Figure 14A:
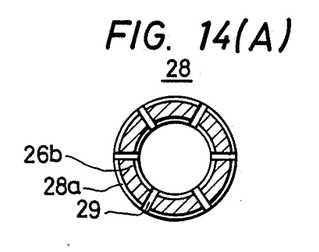
FIG. 14 is an alternative embodiment of a vibrator illustrated in FIG. 11.
Figure 14B:
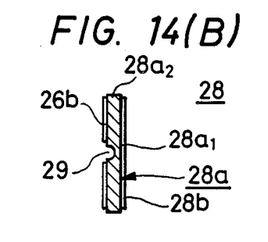

FIG. 14 is a view illustrating a construction of a vibrator 28 in another embodiment of the present invention FIG. 14(A) shows the top surface of the vibrator 18, and FIG. 14(B) illustrates the side face thereof. The vibrator 28 includes an annular plate-like piezoelectric substrate 28a. The substrate 28a has three sets of grooves 29 formed along three rectilinear lines converging at the center of the substrate. The substrate 28a is composed of six pieces of thin portions 28a1 sectioned by the grooves 29 and six pieces of thick portions 28a2 which are respectively contiguous to each of the thin portions. An electrode 26b is formed on each upper surface of the thick portions 28a2, and an annular electrode 28b is formed on the underside of the substrate 28a In the vibrator 28, the thick portions 28a are connected through the thin portions 28a1 to each other. In this embodiment, the forces of thermal deformation which are produced in the mechanical vibration part consisting of the vibrator 28 and the vibratory member 1 are larger than those in FIG. 10 but smaller than those in FIG. 6. As a result, the transducer has less error due to temperature variations When vibrator 28 is used the six thick portions 28a2 are not separated from each other, so that it is easy to manufacture the vibration type transducer.

In the above-described embodiments illustrated in FIGS. 10 and 14, vibrators 26 and 28 are formed by annularly disposing the six pieces of split piezoelectric elements each assuming the circular arc configuration, and the adjacent split piezoelectric elements are completely separated from each other, or these elements are connected through the thin connecting portions to each other. Furthermore, the flexural vibrations of the bottom 1a of the vibratory member 26 or 28 are caused by the five pieces of split piezoelectric elements; and the electrode formed on the remaining one among the six pieces of split piezoelectric elements contributes to the detection of voltage. The present invention is not, however, confined to the number and configuration of the split piezoelectric elements. There may be varied the number of the split piezoelectric elements for causing the flexural vibration of the bottom 1a of the vibratory member and of the split piezoelectric elements on which the electrodes for detecting the voltage are formed. In addition, the configuration of the split piezoelectric element may be rectangular.

According to the embodiments shown in FIGS. 6, 9, 10 and 14, the mass of the mechanical vibration part consisting of the vibratory plate and the piezoelectric vibrator is smaller than that of the mechanical vibration part of the prior art transducer using the disk-like piezoelectric vibrator, and thereby the sensitivity in measurement of the density is improved.

Particularly in the embodiments of FIGS. 10 and 14, even if there exists a difference in coefficient of thermal expansion between the vibratory plate and the piezoelectric elements which are combined to form the vibrator, the forces of thermal deformation with respect to the mechanical vibration part which are created due to the difference in coefficient of thermal expansion and to the variation in temperature of the fluid to be measured are small as compared with the case where the vibrator is composed of a piece of ring-like piezoelectric element. Consequently, an amount of thermal deformation in the mechanical vibration part is reduced, thereby reducing the error due to temperature variations.

Figure 15:
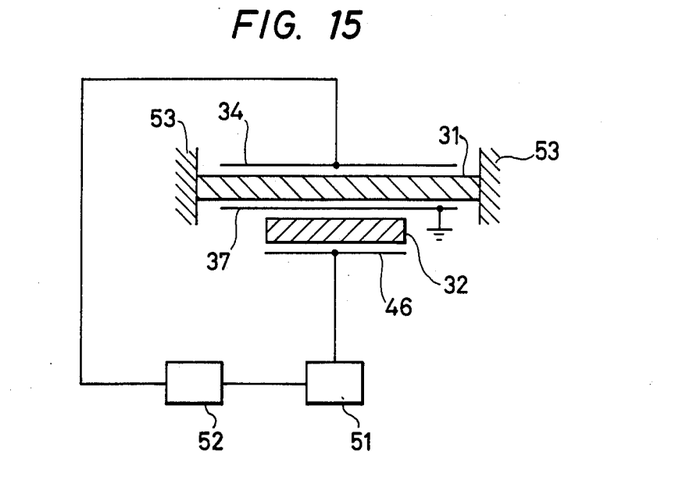
FIG. 15 is a view illustrating a vibratory member in a fourth embodiment of the present invention.

Turning attention to FIG. 15, a vibratory member in a fourth embodiment of the present invention is illustrated. This vibratory member consists of a piezoelectric vibrator formed by conjunctively laminating a first piezoelectric substrate 31 on a second piezoelectric substrate 32. The circumference of the first piezoelectric substrate 31 is secured to a fixing portion 53. An electrode 37 is interposed between the first piezoelectric substrate 31 and the second piezoelectric substrate 32 and is then grounded. An electrode 34 is formed on the other surface of the first piezoelectric substrate 31, while the other surface of the second piezoelectric substrate 32 is provided with an electrode 46.

The first piezoelectric substrate 31 is comprised of a disk (or an elliptical plate) having a large diameter wherein the circumference thereof is fixed to a secured portion 53. The second piezoelectric substrate 32 is composed of a disk having a small diameter. When an AC voltage is applied between the electric 37 and 46, the second piezoelectric substrate 32 is arranged to expand and contract in the radial direction.

The circumferential portion of the first piezoelectric substrate 31 is not necessarily secured around the entire periphery thereof.

The AC voltage is applied across the electrodes 37 and 46 of the second piezoelectric substrate 32 by means of an amplifier 51, at which time the second piezoelectric substrate 32 expands and contracts in the radial direction. When the expansion and contraction of the second piezoelectric substrate 32 takes place, the first piezoelectric substrate 31 is flexed because the circumference thereof is fixed. As a result, the first piezoelectric substrate 31 vibrates in the direction perpendicular to the surface thereof. On the other hand, if the first piezoelectric substrate 31 is polarized, an AC voltage corresponding to the vibration is generated between the electrodes 37 and 34. The phase of the AC voltage generated between electrodes 37 and 34 leads the AC voltage impressed on the second piezoelectric substrate 32 by 90° at a mechanical resonant frequency determined by the piezoelectric vibrator composed of the first piezoelectric substrate 31 and the second piezoelectric substrate 32 and by added mass of a medium coming in contact with this piezoelectric vibrator. Consequently, a positive feedback through a positive feedback circuit 52 to the second piezoelectric substrate 32 is effected by compensating for the above-mentioned phase, whereby the piezoelectric vibrator consisting of the first and second piezoelectric substrates 31 and 32 performs the self-vibrations at the resonant frequency.

Figure 16:
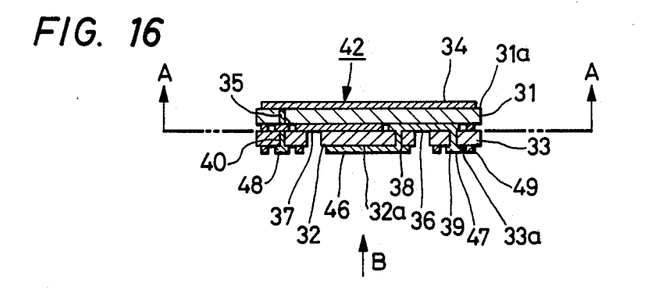
FIG. 16 is a longitudinal cross-sectional view of a vibratory member according to the fourth embodiment generally illustrated in FIG. 15.
Figure 17:
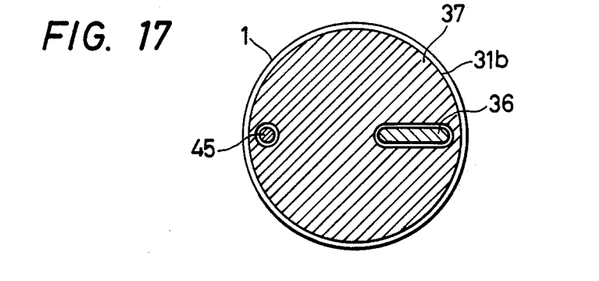
FIG. 17 is a sectional view taken substantially along the line A—A of FIG. 16.
Figure 18:
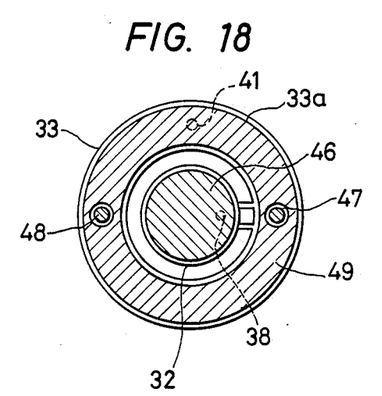
FIG. 18 is a view of the vibratory member of FIG. 16 taken in the direction of an arrow B.

FIG. 16 is a sectional view illustrating an embodiment of the vibratory member generally illustrated in FIG. 15. FIG. 17 is a sectional view taken substantially along the line A—A of FIG. 16. FIG. 18 is a top view taken in the direction indicated by an arrowhead B.

The numeral 31 denotes a first disk-like thin piezoelectric substrate formed from a piezoelectric material which has a thickness of approximately 0.1 mm. One surface 31a of the first piezoelectric substrate 31 is substantially concentrically formed with an electrode 34. The other surface 31b of the first piezoelectric substrate 31 is, as seen from FIG. 17, provided with: an electrode 45 electrically connected via a through-hole 35 formed in the first piezoelectric substrate 31 to the electrode 34; an electrode 36 electrically isolated from the electrode 45; and an electrode 37 electrically isolated from the electrodes 45 and 36, this electrode 37 being formed to cover nearly the whole surface of the other surface 31b of the first piezoelectric substrate 31.

A disk-like thin second piezoelectric substrate 32 formed from the piezoelectric material which has a thickness of approximately 0.1 mm is laminated on electrode 37 to be bonded thereto. The second piezoelectric substrate 32 is formed from the same material as that of the first piezoelectric substrate 31. An annular spacer 33 is bonded to electrode 37 surrounding second piezoelectric substrate 32. An electrode 46 connected via a through-hole 38 to the electrode 36 is substantially concentrically formed on one surface 32a of the second piezoelectric substrate 32.

The annular spacer 33 is formed from the same material as that of second piezoelectric substrate 32 and further has the same thickness as that of this substrate 32. One surface 33a of spacer 33 is formed with an electrode 47 connected via a through-hole 39 to the electrode 36 and with an electrode 48 connected via a through-hole 40 to an electrode 45. An electrode 49 connected via a through-hole 41 to the electrode 37 is provided on surfaces 33a separate from electrodes 47 and 48. The three layer laminate consists of the electrode 34 formed on surface 31a of first piezoelectric substrate 31, electrode 37 formed on the other surface 31b of the first piezoelectric substrate 31 and the electrode 46 formed on the surface 32a of the second piezoelectric substrate 32 which are individually connected via the through-holes 35, 40, 38 and 41 to one surface of the annular spacer 33.

The numeral 42 designates a piezoelectric vibrator which is comprised of the first piezoelectric substrate 31, the second piezoelectric substrate 32 and the spacer 33. Technology of manufacturing a ceramic multilayer wiring substrate can be applied to production of the above-described piezoelectric substrate 42. Namely, electrode patterns are formed by screen printing on the individual surfaces 31a, 31b, 32a and 33a of the first piezoelectric substrate 31, the second piezoelectric substrate 32 and the spacer 33 which are formed of thin films by the green sheet method. After the patterns have been punched out in predetermined shapes, they are laminated.

The sintering of ceramic and the baking of electrode are simultaneously effected. Subsequently, mechanical junction between the first piezoelectric substrate 31, the second piezoelectric substrate 32 and the spacer 33 and electrical junction between the electrodes are simultaneously carried out. DC electric fields are applied between the electrodes 34 and 37 and between the electrodes 36 and 37 of the conjunctively formed vibrator 42, thus performing a so-called polarizing process. As a result, the first piezoelectric substrate 31 and the second piezoelectric substrate 32 are invested with piezoelectric properties. The spacer 33 is not, however, polarized because of the presence of the electrodes 37 and 49 formed on the surface and underside thereof which become conductive via the through-hole 41.

Figure 19:
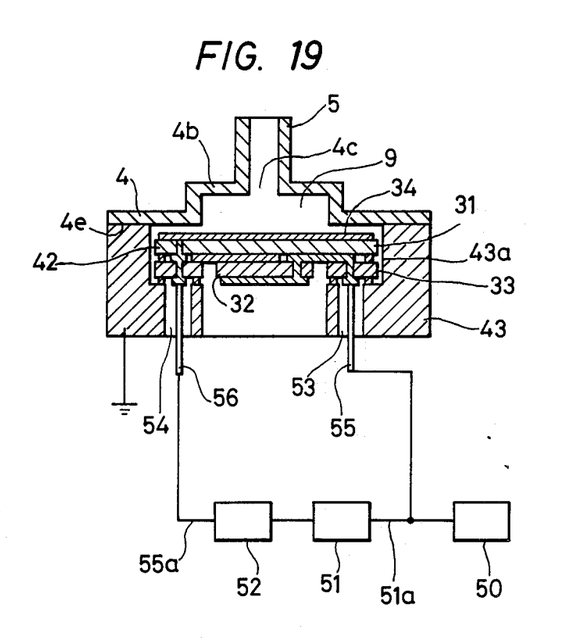
FIG. 19 is a cross-sectional view of a vibration type transducer utilizing the transducer illustrated in FIG. 16.

FIG. 19 illustrates a fourth embodiment of the vibration type transducer according to the present invention which employs the piezoelectric vibrator shown in FIGS. 16 through 18. In FIG. 19, a housing generally indicated at 43 serves to retain the vibrator 42. The housing 43 is formed from a Ni-Fe alloy the thermal expansion coefficient of which is nearly equal to that of the piezoelectric material from which the vibrator 42 is made. The housing 43 which retains the vibrator 42 includes a stepped portion 43a electrically connected to an electrode 49 provided on a spacer 33 by soldering or by connecting means such as a conductive adhesive agent.

The housing 43 is formed with openings 53 and 54 corresponding to electrodes 47 and 48 but is isolated from these electrodes. A depth of the stepped portion 43a is slightly greater than a thickness h of the vibrator 42 so that the vibrator 42 does not jut out Lead wires generally indicated at 55 and 56 are connected to the electrodes 47 and 48.

The numeral 4 stands for a container having a bottom 4b the outer surface of which is fixed to one end of a tube 5. A bottom 4b is formed with a through-hole 4c communicating with the inside of tube 5. A surface 4e on the side of the opening is hermetically joined to the end surface of housing 43, and a small air gap is formed between the electrode 34 of the vibrator 42 and surface 4e. It is to be noted that container 4 is shaped from the same material as that of housing 43. Container 4, a cavity 9 formed between bottom 4b and piezoelectric vibrator 42 and a medium within the tube 5 cooperate to constitute an acoustic vibration system, the arrangement being such that only the mass of the medium within the tube 5 acts as additional mass to the vibrator 42 for sufficiently increasing a spring constant of the medium of the cavity 9.

The numeral 51 denotes an amplifier for applying an AC voltage through the electrodes 47, 36 and 46 to the second piezoelectric substrate 32. The numeral 52 represents a feedback circuit for permitting a voltage generated in the first piezoelectric substrate 31 to be positively fed back to the amplifier 51 after detecting the voltage through the electrodes 34, 45 and 48.

The second piezoelectric substrate 32 is, as discussed above, arranged to expand and contract in the radial direction when an AC voltage is applied between the electrodes 37 and 46. When the expansion and contraction of the second piezoelectric substrate 32 take place, first piezoelectric substrate 31 flexes, whereby the first piezoelectric substrate 31 vibrates in the direction perpendicular to the surface thereof. As mentioned earlier, the first piezoelectric substrate 31 is polarized, an AC voltage corresponding to the vibration is generated across the electrodes 37 and 34. The phase of this AC voltage leads the AC voltage applied to the second piezoelectric vibrator 42 consisting of the first and second piezoelectric substrates 31 and 32 by 90° and the added mass of the medium within the tube 5. Hence, the positive feedback to the second piezoelectric substrate 32 is compensates for the above-mentioned phase, and the piezoelectric vibrator 42 oscillates at the resonant frequency. It is therefore possible to measure the added mass of the medium, i.e., the density (or pressure) by measuring this frequency in a detecting circuit 50.

In this vibration type transducer, as discussed above, the first piezoelectric substrate 31 of vibrator 42 is formed from material identical with that of the piezoelectric substrate 32 and is also polarized under the same conditions. Consequently, it is feasible to eliminate the error in rate of thermal expansion between the first piezoelectric substrate 31 and the second piezoelectric substrate 32 over a wide range of temperatures. It is also possible to prevent a variation in resonant frequency of the vibrator 42 due to the difference in thermal expansion between the two substrates. Moreover, highly accurate density measurements can be made. The electrode for applying the AC voltage to the piezoelectric substrate 32, the electrode for detecting the vibrations of the piezoelectric substrate 31 and the lead wire portions are formed in accordance with circuit patterns. The wire portions extend out onto one surface and to the circumference, defined as the fixed portion, of the vibrator 42 by connecting each of them through the through-holes. This vibration transducer therefore provides additional advantages in which the electrical connection can be facilitated, the lead wires are free from vibrational stress Referring to FIG. 20, a vibratory member used in a fifth embodiment of the present invention is illustrated. This vibratory member is composed of a piezoelectric vibrator formed by conjunctively laminating the first piezoelectric substrate 31 on the second piezoelectric substrate 32. The circumference of one surface of the first piezoelectric substrate 31 is secured to a fixing portion 53. An electrode 37 is provided between the first piezoelectric substrate 31 and the second piezoelectric substrate 32, this electrode 37 is grounded. An electrode 34 is formed on the other surface of the first piezoelectric substrate, while an electrode 46 is formed on the other surface of the second piezoelectric substrate 32. In this case, the first piezoelectric substrate 31 is composed of a disk (or elliptical plate) having a large diameter, and the circumference of one surface thereof is fixed to the fixing portion 53. While on the other hand, the second piezoelectric substrate 32 is composed of a disk having a small diameter. Upon an application of an AC voltage between the electrodes 37 and 34, the first piezoelectric substrate 31 expands and contracts in the radial direction. It is not required that the fixation of the first piezoelectric substrate 31 is secured around the entire circumference thereof When the AC voltage is applied by means of the amplifier 51 between electrodes 37 and 34 of the first piezoelectric substrate 31, the expanding and contracting forces act in the radial direction. Since the circumference of one surface of substrate 31 is fixed the amount of flex is dependent on the expansion and contraction forces and to the surface area fixed along the circumference. The resultant vibration of piezoelectric substrate 32 generates an AC voltage across the electrodes 37 and 46. This AC voltage leads the AC voltage applied on the second piezoelectric substrate 32 by 90° mechanical resonant frequency determined by the piezoelectric vibrator consisting of the first and second piezoelectric substrates 31 and 32 and by added mass of a medium being in contact with the piezoelectric vibrator. Positive feedback via a positive feedback circuit 52 to the first piezoelectric substrate 31 compensates the foregoing phase lead, whereby the piezoelectric vibrator consisting of the first and second piezoelectric substrates 31 and 32 performs oscillations at the resonant frequency.

Figure 20:
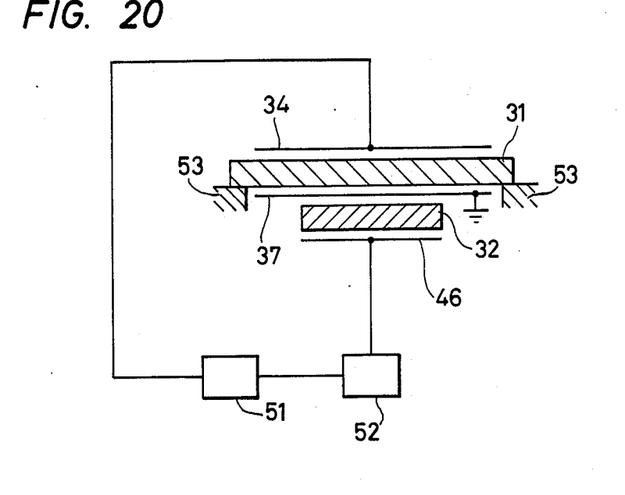
FIG. 20 is a view of a vibratory member according to a fifth embodiment of the present invention.
Figure 21:
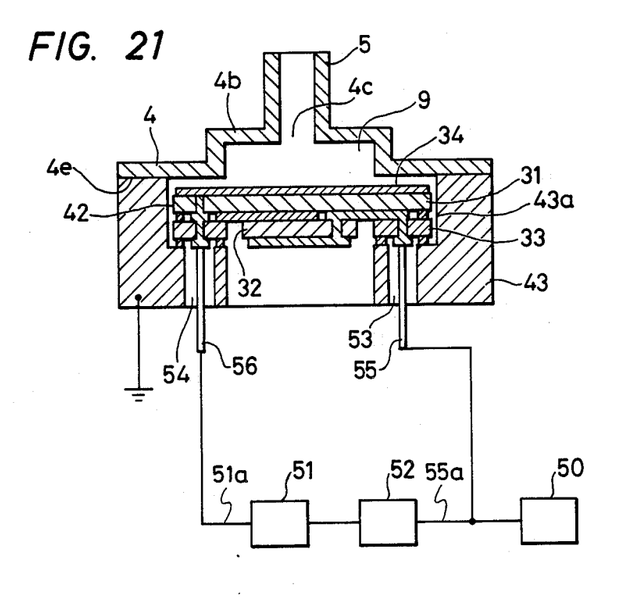
FIG. 21 is a longitudinal cross-sectional view of the vibration type transducer illustrated in FIG. 20.

Referring to FIG. 20, there is illustrated the principal elements of a piezoelectric vibrator. The piezoelectric vibrator may have the same construction as that of the piezoelectric vibrator shown in FIG. 18 but of course will operate differently. FIG. 21 shows the fifth embodiment of the present invention which operates according to the basis of the principle of FIG. 20 by employing the piezoelectric vibrator illustrated in FIGS. 16 through 18.

In FIG. 21, the components having the same functions as those of the respective components shown in FIG. 19 are marked with like numerals In FIG. 21, as described above, upon an application of the AC voltage between the electrodes 37 and 34 by means of the amplifier 51, the first expansion and contraction of the plate thickness works against the fixing portion of the piezoelectric substrate 31, thereby causing vibrations in the direction perpendicular to the surface thereof. Meanwhile, the second piezoelectric substrate 32 is also polarized as in the previous case, and hence an AC voltage corresponding to the foregoing vibration is generated between the electrodes 37 and 46. The phase of the AC voltage generated by substrate 32 leads the AC voltage applied to the piezoelectric substrate 32 by 90° at a mechanical resonant frequency determined by the piezoelectric vibrator 42 consisting of the first and second piezoelectric substrates 31 and 32 and by added mass of the medium within tube 5. Positive feedback via a feedback circuit 52 to the second piezoelectric substrate 32 compensates the above-mentioned phase, whereby the piezoelectric vibrator 42 oscillates at the resonant frequency. It is therefore possible to measure the added mass of the medium, viz., the density (or pressure), by measuring the frequency with a detecting circuit 50.

According to the embodiments illustrated in FIGS. 19 and 21, the expansion of the first piezoelectric substrate can be substantially equated to that of the second piezoelectric substrate, so that it is possible to prevent a variation in resonant frequency of the vibrator which is associated with the thermal deformation caused by a difference in the rate of thermal expansion.

In these embodiments, the electrode of the two-layered piezoelectric substrates, the electrode for applying the voltage to the former electrode and the lead electrode for feeding the voltage out of this electrode are led out via the through-holes formed in the piezoelectric substrates onto one surface of any one of the two piezoelectric substrate and further to the circumference, defined as the fixing portion, of the vibrator. This arrangement contrasts the conventional way in which a connection with the circuit is made by employing the lead wires directly led from the vibrating parts. Therefore, the following effects are produced. There is no variation in resonant frequency of the vibrator by the mass of the lead wire and by the resonance thereof, and the cost of production can be reduced.

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. An apparatus for detecting the resonant frequency of a vibratory member in contact with a fluid, comprising:
    a housing having an interior chamber;
    a vibratory member having a first and second side mounted in said housing, said vibratory member disposed in said interior chamber to define a first internal cavity an to prevent flow communication of fluid between said first side of said vibratory member to said second side;
    a first fluid inlet means for introducing a fluid into said first chamber;
    a vibratory controller for controlling and responding to said vibratory member; and
    said vibratory member including a first fixedly held substantially planar piezoelectric device and a second substantially planar piezoelectric device secured together in planar relationship and operatively coupled to said vibratory controller so that said vibratory controller detects the resonant frequency of said vibratory member.

2. An apparatus according to claim 1 wherein said second piezoelectric device is responsive to said vibratory controller for producing flexural vibrations in said first and second piezoelectric devices.

3. An apparatus according to claim 2, wherein said vibratory controller is responsive to signals generated by said first piezoelectric device during flexural vibrations for determining the resonant frequency of said vibratory member in contact with a fluid and producing control signals to regulate the vibrations of said first and second piezoelectric devices.

4. An apparatus according to claim 3, wherein said vibratory member is fixedly held substantially at the circumference thereof.

5. A method for measuring the resonant frequency of a vibratory member in a cavity having a fluid inlet means, the vibratory member in contact with the fluid including a first fixedly held substantially planar piezoelectric device and a second substantially planar piezoelectric device secured together in a planar relationship, comprising the steps of:
    applying a first voltage having a first frequency to said second piezoelectric device for vibrating said second piezoelectric device and said first piezoelectric device;
    producing signals from said vibrating second piezoelectric device in response to the vibration thereof;
    regulating said first frequency as a function of said signals produced for obtaining the resonant frequency of the vibratory member; and
    detecting the resonant frequency of the vibratory member.

* * * * *

UNITED STATES PATENT AND TRADEMARK OFFICE
CERTIFICATE OF CORRECTION

PATENT NO.    : 4,961,345
DATED         : October 09, 1990
INVENTOR(S)   : Michihiko Tsuruoka et al.

It is certified that error appears in the above-identified patent and that said Letters Patent is hereby corrected as shown below:

Claim 1, Column 15, Line 42, change "an" to --and--.

Signed and Sealed this

First Day of September, 1992

Attest:

DOUGLAS B. COMER

*Attesting Officer*    *Acting Commissioner of Patents and Trademarks*